United States Patent
Moser et al.

(10) Patent No.: US 11,066,408 B2
(45) Date of Patent: Jul. 20, 2021

(54) CRYSTALLINE BINARY SODIUM SALTS OF 5-METHYL-(6S)-TETRAHYDROFOLIC ACID WITH ORGANIC BASES

(71) Applicant: MERCK PATENT GMBH, Darmstadt (DE)

(72) Inventors: Rudolf Moser, Schaffhausen (CH); Viola Groehn, Dachsen (CH); Fritz Blatter, Reinach (CH); Martin Szelagiewicz, Basel (CH); Ruth Boehni Stamm, Stein Am Rhein (CH); Markus Ruettimann, Winterthur (CH); Giuseppe Lapadula, Basel (CH)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 16/499,671

(22) PCT Filed: Mar. 28, 2018

(86) PCT No.: PCT/EP2018/057902
§ 371 (c)(1),
(2) Date: Sep. 30, 2019

(87) PCT Pub. No.: WO2018/178142
PCT Pub. Date: Oct. 4, 2018

(65) Prior Publication Data
US 2020/0039982 A1 Feb. 6, 2020

(30) Foreign Application Priority Data
Mar. 31, 2017 (EP) .................................... 17164346

(51) Int. Cl.
*C07D 475/04* (2006.01)
*A23L 33/16* (2016.01)
*A61K 31/519* (2006.01)
*C07C 215/08* (2006.01)
*C07D 295/088* (2006.01)

(52) U.S. Cl.
CPC ............ *C07D 475/04* (2013.01); *A23L 33/16* (2016.08); *A61K 31/519* (2013.01); *C07C 215/08* (2013.01); *C07D 295/088* (2013.01); *A23V 2002/00* (2013.01); *C07B 2200/13* (2013.01)

(58) Field of Classification Search
None
See application file for complete search history.

(56) References Cited

U.S. PATENT DOCUMENTS

| | | |
|---|---|---|
| 6,441,168 B1 | 8/2002 | Müller et al. |
| 2009/0209543 A1 | 8/2009 | Valoti et al. |
| 2016/0207925 A1 | 7/2016 | Fracchia |

OTHER PUBLICATIONS

Berry et al., Advanced Drug Delivery Reviews, 2017, 117, 3-24.
International Search report PCT/EP2018/057902 dated May 29, 2018 (pp. 1-2).

*Primary Examiner* — Joseph R Kosack
(74) *Attorney, Agent, or Firm* — Millen White Zelano and Branigan, PC; Csaba Henter

(57) ABSTRACT

The present invention is directed to crystalline salt of 5-methyl-(6S)-tetrahydrofolic acid comprising
(i) 5-methyl-(6S)-tetrahydrofolic acid,
(ii) sodium and
(iii) an organic base having a pKa value from 6 to 11;
wherein the molar ratio of 5-methyl-(6S)-tetrahydrofolic acid to the sodium is from 1:0.5 to 1:1.5 and the molar ratio of 5-methyl-(6S)-tetrahydrofolic acid to the organic base is 1:0.5 to 1:1.5 and/or hydrates and/or solvates thereof, as well as, a processes of obtaining the same.

29 Claims, 5 Drawing Sheets

CRYSTALLINE BINARY SODIUM SALTS OF 5-METHYL-(6S)-TETRAHYDROFOLIC ACID WITH ORGANIC BASES

The present invention is directed to a crystalline sodium salt of 5-methyl-(6S)-tetrahydrofolic acid, (N-[4-[[(2-amino-1,4,5,6,7,8-hexahydro-5-methyl-4-oxo-(6S)-pteridinyl)methyl]amino]benzoyl]-L-glutamic acid, herein abbreviated as MTHF, comprising sodium and an organic base having a pKa value from 6 to 11, as well as, a process of obtaining the same.

Tetrahydrofolates are predominantly used as 5-formyltetrahydrofolic acid and the salts thereof (leucovorin and levoleucovorin), as 5-methyltetrahydrofolic acid and the salts thereof (Metafolin®), or as 5,10-methylenetetrahydrofolic acid and the salts thereof (Modufolin®) for the treatment of megaloblastic folic acid anaemia, as an antidote for increasing the compatibility of folic acid antagonists, particularly of aminopterin and methotrexate in cancer therapy ("antifolate rescue"), for increasing the therapeutic effect of fluorinated pyrimidines and for the treatment of autoimmune diseases such as psoriasis and rheumatoid arthritis, for increasing the compatibility of certain antiparasitic for mutations, for instance trimethoprim-sulfamethoxazole, and for reducing the toxicity of dideazatetrahydrofolates in chemotherapy.

5-Methyltetrahydrofolic acid is used in particular as a drug and as a food additive, as a vitamin preparation, for the prevention of neural tube defects, for the treatment of depressive illnesses, and for influencing the homocysteine level.

5-Methyltetrahydrofolic acid and salts thereof are extremely unstable and in particular are highly susceptible to oxidation [see also A. L. Fitzhugh, Pteridines 4 (4), 187-191 (1993) in this respect] and are therefore difficult to produce at a level of purity which is acceptable for a pharmaceutical active ingredient or a food additive.

Various methods, such as excluding oxygen as completely as possible or the addition of antioxidants such as ascorbic acid or reduced L-glutathione, have been employed in order to overcome the instability of 5-methyltetrahydrofolic acid.

U.S. Pat. No. 6,441,168 B1 discloses alkaline earth salts of 5-methyltetrahydrofolic acid, particularly the calcium salt, its crystallization and its use. The crystalline calcium salts of 5-methyl-(6S)-tetrahydrofolic acid exist in four different crystalline modifications.

The drawback of the calcium salts of 5-methyl-(6S)-tetrahydrofolic acid is that they exist in four modifications, since the process of manufacturing each of which has to be controlled very precisely. Additionally, the solubility of said calcium salt of 5-methyl-(6S)-tetrahydrofolic acid in water is relatively poor, possibly leading to a reduced bioavailability and a limitation to its applicable form of use. Also a low solubility is resulting in low time-volume yields when needing to dissolve such compound for further processing e.g. a purification by recrystallization. Additionally the crystalline salts of 5-methyl-(6S)-tetrahydrofolic acid of U.S. Pat. No. 6,441,168 B1 also are having a water of crystallization of at least one equivalent per equivalent of 5-methyltetrahydrofolic acid.

New crystal forms of a pharmaceutically useful compound offer an opportunity to improve the performance profile of a pharmaceutical and/or vitamin/medical food products. It widens the reservoir of materials a formulation scientist has available for designing new dosage forms with improved characteristics.

The technical problem underlying the present invention is solved by a crystalline salt of 5-methyl-(6S)-tetrahydrofolic acid comprising
(i) 5-methyl-(6S)-tetrahydrofolic acid,
(ii) sodium and
(iii) an organic base having a pKa value from 6 to 11;
wherein the molar ratio of 5-methyl-(6S)-tetrahydrofolic acid to the sodium is from 1:0.5 to 1:1.5 and the molar ratio of 5-methyl-(6S)-tetrahydrofolic acid to the organic base is from 1:0.5 to 1:1.5; and/or hydrates and/or solvates thereof.

Preferably, the molar ratio of 5-methyl-(6S)-tetrahydrofolic acid to the sodium is from 1:0.75 to 1:1.25 and the molar ratio of 5-methyl-(6S)-tetrahydrofolic acid to the organic base is from 1:0.75 to 1:1.25 and even more preferred, the molar ratio of 5-methyl-(6S)-tetrahydrofolic acid to the sodium is approximately 1:1 and the molar ratio of 5-methyl-(6S)-tetrahydrofolic acid to the organic base is approximately 1:1.

Preferably, the crystalline sodium salt of 5-methyl-(6S)-tetrahydrofolic acid (MTHF) comprising an organic base having a pKa value from 6 to 11 has a molar ratio of 5-methyl-(6S)-tetrahydrofolic acid to sodium to organic base having a pKa value from 6 to 11 from 1:0.5:0.5 to 1:1.5:1.5 and/or hydrates and/or solvates thereof.

Preferably, the crystalline salt has a molar ratio of 5-methyl-(6S)-tetrahydrofolic acid to sodium to organic base is from 1:0.75:0.75 to 1:1.25:1.25.

Even more preferred, the crystalline salt has a molar ratio of 5-methyl-(6S)-tetrahydrofolic acid to sodium to organic base of approximately 1:1:1.

The solid form of the present invention possesses improved pharmacological characteristics, for example, improved bioavailability, thus offering enhanced possibilities to modulate and design improved drug products.

Additionally, only one crystalline modification of the sodium salt of 5-methyl-(6S)-tetrahydrofolic acid and organic base exists, thus, leading to an improved and accurate process of obtaining the same.

Preferably, the organic base is selected from the group consisting of 4-(2-hydroxyethyl)-morpholine, 1-(2-hydroxyethyl)-pyrrolidine, 2-dimethylaminoethanol imidazole, 2-dimethylaminoethanol, and tert-butylamine, and mixtures thereof.

Preferably, the crystalline salt of the present invention is the sodium salt of 5-methyl-(6S)-tetrahydrofolic acid comprising 4-(2-hydroxyethyl)-morpholine and has a PXRD pattern with at least one characteristic peak (expressed in 2θ±0.2° 2θ (CuKα radiation)) at 14.1, 15.8, 16.2, 16.6, 18.2, 19.9, 21.8, and 25.0.

Preferably, the crystalline salt of the present invention is the sodium salt of 5-methyl-(6S)-tetrahydrofolic acid comprising 4-(2-hydroxyethyl)-morpholine having a PXRD pattern with at least two, even more preferred at least three, most preferred at least four, preferably at least five, more preferred at least six, even more preferred at least seven and most preferred all of the characteristic peaks (expressed in 2θ±0.2° 2θ (CuKα radiation)) at 14.1, 15.8, 16.2, 16.6, 18.2, 19.9, 21.8, and 25.0.

Even more preferred, the sodium salt of 5-methyl-(6S)-tetrahydrofolic acid comprising 4-(2-hydroxyethyl)-morpholine has a PXRD pattern with at least one characteristic peak (expressed in 2θ±0.2° 2θ (CuKα radiation)) at 8.3, 13.9, 14.1, 14.2, 15.5, 15.8, 16.2, 16.6, 18.2, 19.4, 19.6, 19.9, 20.1, 20.8, 21.8, 23.6, 23.9, 25.0, 25.9, 28.1, 28.5, and 29.6 and most preferred the sodium salt of 5-methyl-(6S)-tetrahydrofolic acid and 4-(2-hydroxyethyl)-morpholine has a PXRD pattern substantially as shown in FIG. 1.

Even more preferred, the sodium salt of 5-methyl-(6S)-tetrahydrofolic acid comprising 4-(2-hydroxyethyl)-morpholine has a PXRD pattern with at least two, even more preferred at least three, most preferred at least four, preferably at least five, more preferred at least six, most preferred at least seven and even more preferred all of the characteristic peaks (expressed in 2θ±0.2° 2θ (CuKα radiation)) at 8.3, 13.9, 14.1, 14.2, 15.5, 15.8, 16.2, 16.6, 18.2, 19.4, 19.6, 19.9, 20.1, 20.8, 21.8, 23.6, 23.9, 25.0, 25.9, 28.1, 28.5, and 29.6.

A further aspect of the invention is the crystalline sodium salt of 5-methyl-(6S)-tetrahydrofolic acid comprising 4-(2-hydroxyethyl)-morpholine having a Raman spectrum with least one characteristic peak (expressed in wavenumbers, cm$^{-1}$, with an experimental uncertainty of ±1-2 cm$^{-1}$) at: 2954, 2875, 1610, 1582, 1547, 1482, 1463, 1419, 1340, 1293, 1217, 1184, 1154, 1069, 1023, 946, 892, 861, 836, 778, 649, 638, 624, 479, 415 and 374 cm$^{-1}$.

Yet a further aspect of the invention is the crystalline sodium salt of 5-methyl-(6S)-tetrahydrofolic acid comprising 4-(2-hydroxyethyl)-morpholine which exhibits a Raman spectrum substantially as depicted in FIG. 2.

Additionally, one crystalline modification of the sodium salt of 5-methyl-(6S)-tetrahydrofolic acid and 4-(2-hydroxyethyl)-morpholine exists, thus, leading to an improved and accurate process of obtaining the same.

Preferably, the crystalline salt is the sodium salt of 5-methyl-(6S)-tetrahydrofolic acid comprising 1-(2-hydroxyethyl)-pyrrolidine and has a PXRD pattern with at least one characteristic peak (expressed in 2θ±0.2° 2θ (CuKα radiation)) at 8.3, 14.3, 14.4, 15.6, 16.0, 16.7, 18.5, 20.0, 21.8, and 25.2.

Preferably, the crystalline salt is the sodium salt of 5-methyl-(6S)-tetrahydrofolic acid comprising 1-(2-hydroxyethyl)-pyrrolidine and has a PXRD pattern with at least two, even more preferred at least three, most preferred at least four, preferably at least five, more preferred at least six, even more preferred at least seven and most preferred all of the characteristic peaks (expressed in 2θ±0.2° 2θ (CuKα radiation)) at 8.3, 14.3, 14.4, 15.6, 16.0, 16.7, 18.5, 20.0, 21.8, and 25.2.

Preferably, the crystalline salt is the sodium salt of 5-methyl-(6S)-tetrahydrofolic acid comprising 1-(2-hydroxyethyl)-pyrrolidine and has a PXRD pattern with at least two, even more preferred at least three, most preferred at least four, preferably at least five, more preferred at least six, most preferred at least seven and even more preferred all of the characteristic peaks (expressed in 2θ±0.2° 2θ (CuKα radiation)) at 4.8, 8.3, 12.5, 13.6, 14.3, 14.4, 15.6, 16.0, 16.1, 16.7, 18.3, 18.5, 19.6, 20.0, 20.7, 21.8, 22.3, 22.7, 23.8, 24.0, and 25.2.

Preferably, the crystalline salt is the sodium salt of 5-methyl-(6S)-tetrahydrofolic acid comprising 1-(2-hydroxyethyl)-pyrrolidine has a PXRD pattern substantially as shown in FIG. 6.

A further aspect of the invention is the crystalline sodium salt of 5-methyl-(6S)-tetrahydrofolic acid and 1-(2-hydroxyethyl)-pyrrolidine which has a Raman spectrum with least one characteristic peak (expressed in wavenumbers, cm$^{-1}$, with an experimental uncertainty of ±1-2 cm$^{-1}$) at 3058, 2954, 2875, 1611, 1583, 1548, 1529, 1480, 1464, 1419, 1341, 1295, 1272, 1216, 1183, 1155, 1068, 947, 890, 861, 836, 779, 648, 637, 624, 480, 416 and 375 cm$^{-1}$.

A further aspect of the invention is the crystalline sodium salt of 5-methyl-(6S)-tetrahydrofolic acid and 1-(2-hydroxyethyl)-pyrrolidine which exhibits a Raman spectrum substantially as shown in FIG. 7.

Additionally, one crystalline modification of the sodium salt of 5-methyl-(6S)-tetrahydrofolic acid and 1-(2-hydroxyethyl)-pyrrolidine exists, thus, leading to an improved and accurate process of obtaining the same.

Preferably, the crystalline salt of the present invention is the sodium salt of 5-methyl-(6S)-tetrahydrofolic acid comprising 2-dimethylaminoethanol and having a PXRD pattern with at least one characteristic peak (expressed in 2θ±0.2° 2θ (CuKα radiation)) at 8.3, 13.6, 14.2, 14.4, 15.8, 16.7, 18.5, 19.8, 19.9, 24.0, 25.1, and 30.2.

Even more preferred, the crystalline salt of the present invention is the sodium salt of 5-methyl-(6S)-tetrahydrofolic acid comprising 2-dimethylaminoethanol and having a PXRD pattern with at least two, even more preferred at least three, most preferred at least four, preferably at least five, more preferred at least six, even more preferred at least seven and most preferred all of the characteristic peaks (expressed in 2θ±0.2° 2θ (CuKα radiation)) at 8.3, 13.6, 14.2, 14.4, 15.8, 16.7, 18.5, 19.8, 19.9, 24.0, 25.1, and 30.2

Preferably, the crystalline salt is the sodium salt of 5-methyl-(6S)-tetrahydrofolic acid comprising 2-dimethylaminoethanol and having a PXRD pattern with at least one characteristic peak (expressed in 2θ±0.2° 2θ (CuKα radiation)) at 8.3, 13.6, 14.2, 14.4, 15.7, 15.8, 16.0, 16.7, 17.1, 18.5, 19.8, 19.9, 21.9, 22.1, 22.7, 24.0, 25.1, 25.5, 25.9, 27.8, 28.5 and 30.2.

Even more preferred, the crystalline salt is the sodium salt of 5-methyl-(6S)-tetrahydrofolic acid comprising 2-dimethylaminoethanol and having a PXRD pattern with at least two, even more preferred at least three, most preferred at least four, preferably at least five, more preferred at least six, most preferred at least seven and even more preferred all of the characteristic peaks (expressed in 2θ±0.2° 2θ (CuKα radiation)) at 8.3, 13.6, 14.2, 14.4, 15.7, 15.8, 16.0, 16.7, 17.1, 18.5, 19.8, 19.9, 21.9, 22.1, 22.7, 24.0, 25.1, 25.5, 25.9, 27.8, 28.5 and 30.2.

Preferably, the crystalline salt is the sodium salt of 5-methyl-(6S)-tetrahydrofolic acid 2-dimethylaminoethanol having a PXRD pattern substantially as shown in FIG. 8.

A further aspect of the invention is that the crystalline sodium salt of 5-methyl-(6S)-tetrahydrofolic acid and 2-dimethylaminoethanol having a Raman spectrum with least one characteristic peak (expressed in wavenumbers, cm$^{-1}$, with an experimental uncertainty of ±1-2 cm$^{-1}$) at: 3054, 2955, 2871, 1609, 1580, 1552, 1463, 1420, 1345, 1307, 1272, 1183, 1059, 1023, 948, 890, 864, 836, 777, 649, 637, 480, 414 and 372 cm$^{-1}$.

Preferably, the crystalline sodium salt of 5-methyl-(6S)-tetrahydrofolic acid and 2-dimethylaminoethanol exhibits a Raman spectrum substantially as shown in FIG. 9.

Additionally, one crystalline modification of the sodium salt of 5-methyl-(6S)-tetrahydrofolic acid and 2-dimethylaminoethanol exists, thus, leading to an improved and accurate process of obtaining the same.

Yet a further aspect of the present invention is that the crystalline sodium salt of 5-methyl-(6S)-tetrahydrofolic acid comprising 4-(2-hydroxyethyl)-morpholine can readily be obtained in favorable particulate properties. The salt of this invention can be obtained in large, rod-shape particles that show excellent sedimentation and filtration properties that are useful for separation of the solid product in large scale production (FIG. 3). Contrary thereto the calcium salt of 5-methyl-(6S)-tetrahydrofolic acid according to U.S. Pat. No. 6,441,168 B1 (FIGS. 4, 5) does not crystallize in large, rod-shaped particles, thus, leading to poorer processing properties, since such particles are difficult to handle and difficult to separate from a suspension after crystallization by filtration.

A further aspect of the present invention is a process for obtaining the crystalline sodium salt of 5-methyl-(6S)-tetrahydrofolic acid comprising an organic base having a pKa value from 6 to 11 comprising the steps of:

a) providing of 5-methyl-(6S)-tetrahydrofolic acid, optionally in a suitable solvent or a mixture of solvents;
b) adding sodium hydroxide to the composition of step a);
c) adding an organic base having a pKa value from 6 to 11;
d) optionally adding a solvent or a mixture of solvents to the composition of step b) or step c);
e) crystallizing;
f) optionally adding more solvent or mixture of solvents; and
g) isolating the obtained solid.

Preferably, the molar ratio of 5-methyl-(6S)-tetrahydrofolic acid and sodium hydroxide in step b) is in the range of from 1:0.5 to 1:1.5 and more preferred from 1:0.9 to 1:1.5.

In a further preferred embodiment, the molar ratio of 5-methyl-(6S)-tetrahydrofolic acid and the organic base having a pKa value from 6 to 11 in step c) is in the range of from 1:0.5 to 1:3.

Preferably, the solvent and/or mixtures of solvents according to step a), c) and/or d) is selected from the group consisting of water, water-soluble alcohols, methanol, ethanol, isopropanol, n-propanol, acetonitrile, tetrahydrofuran, acetone, methyl ethyl ketone, methyl isobutyl ketone, benzylalcohol, and mixtures thereof.

Furthermore, steps b) and c) can be interchanged.

Preferably, in step c), d) and/or e) the temperature is less than 60° C., more preferred less than 50° C., even more preferred less than 40° C. and most preferred less than 30° C.

Preferably, in step a), b), c), d) and/or e) seed crystals are added. Even more preferred the seed crystals are the desired sodium salt of 5-methyl-(6S)-tetrahydrofolic acid comprising an organic base having a pKa value from 6 to 11.

Preferably, the organic base of step c) is selected from the group consisting of 4-(2-hydroxyethyl)-morpholine, 1-(2-hydroxyethyl)-pyrrolidine, imidazole, 2-dimethylaminoethanol, and tert-butylamine; and mixtures thereof.

A further aspect of the present invention is a pharmaceutical composition, food additive, vitamin and/or other preparation comprising the crystalline sodium salt of 5-methyl-(6S)-tetrahydrofolic acid comprising an organic base according to the present invention and optionally one or more acceptable excipients and the use of the crystalline sodium salt of 5-methyl-(6S)-tetrahydrofolic acid and the organic base according to the present invention as constituent for the production of drugs, vitamins and/or food additives.

The crystalline sodium salt of 5-methyl-(6S)-tetrahydrofolic acid comprising an organic base of the present invention for use in the treatment of anemia, neural tube defects, cardiovascular diseases, depression, Alzheimer's disease, cognitive impairment and osteoporosis and/or dietary management of low plasma and/or low red blood cell and/or low cerebrospinal fluid and/or low peripheral or central nervous system folate is also part of the present invention.

Surprisingly, the crystalline sodium salts of 5-methyl-(6S)-tetrahydrofolic acid of the present invention have an improved kinetic solubility compared with the crystalline calcium salt disclosed in U.S. Pat. No. 6,441,168 B1. The measurement of the kinetic solubility was conducted as described in the experimental part.

The solubility of the crystalline sodium salt of 5-methyl-(6S)-tetrahydrofolic acid comprising 4-(2-hydroxyethyl)-morpholine of the present invention in water (room temperature) is greater than 54 mg per 1 ml of water, whereas the calcium salt exhibits a solubility being considerably smaller than 10 mg per 1 ml of water. [remark: not assay corrected]

Moreover, the crystalline sodium salt of 5-methyl-(6S)-tetrahydrofolic acid comprising 1-(2-hydroxyethyl)-pyrrolidine also has a solubility greater than 100 mg per 1 ml of water (room temperature).

Additionally, the crystalline sodium salt of 5-methyl-(6S)-tetrahydrofolic acid comprising 2-dimethylaminoethanol also has a solubility greater than 55 mg per 1 ml of water (room temperature).

Due to the higher solubility of the sodium salts of the present invention the bioavailability is much better. This results in oral dosage forms, in which the amount of the active ingredient can be reduced, without diminishing the effectivity of the medicament or food additive.

Surprisingly, each of the above described crystalline sodium salts of 5-methyl-(6S)-tetrahydrofolic acid and an organic base having a pKa value from 6 to 11 of the present invention form only one crystalline form which leads compared with the calcium salts of 5-methyl-(6S)-tetrahydrofolic acid disclosed in U.S. Pat. No. 6,441,168 B1 to a sleek and accurate process of manufacturing which can be controlled very precisely. Said result could not be foreseen by the skilled artisan.

Pharmaceutical compositions according to the present invention can be applied for all modes of administration, preferably for oral, parenteral, intramuscular, intraspinal, intrathecal, peridontal, topical or rectal administration.

EXPERIMENTAL

Powder X-Ray Diffraction:

Stoe Stadi P equipped with a Mythen1K Detector; Cu-Kα1 radiation; standard measurement conditions: transmission; 40 kV and 40 mA tube power; curved Ge monochromator; 0.02°2θ step size, 48 s step time, 1.5-50.5°2θ scanning range; detector mode: step scan; 1°2θ detector step; standard sample preparation: 10 to 20 mg sample was placed between two acetate foils; sample holder: Stoe transmission sample holder; the sample was rotated during the measurement. All sample preparation and measurement was done in an ambient air atmosphere.

Microscopy:

Light microscopy was performed on a Leitz Orthoplan polarized microscope, generally a 10×10 magnification was applied.

TG-FTIR:

Thermogravimetric measurements were carried out with a Netzsch Thermo-Microbalance TG 209 coupled to a Bruker FTIR Spectrometer Vector 22 (sample pans with a pinhole, $N_2$ atmosphere, heating rate 10 K/min).

Raman Spectroscopy:

FT-Raman spectra were recorded on a Bruker MultiRAM FT-Raman or a Bruker RFS 100 FT-Raman system with a near infrared Nd:YAG laser operating at 1064 nm and a liquid nitrogen-cooled germanium detector. 64 scans with a resolution of 2 $cm^{-1}$ were accumulated in the range from 3500 to −50 $cm^{-1}$; however, only data above 100 $cm^{-1}$ are evaluated due to filter cutoff effects. Nominal laser powers are typically 100 or 300 mW.

Example 1: Preparation of the Crystalline Sodium Salt of 5-methyl-(6S)-tetrahydrofolic Acid and Comprising 4-(2-hydroxy-ethyl)-morpholine To 468 mg of 5-methyl-(6S)-tetrahydrofolic acid monohydrate (assay 5-methyltetrahydrofolic acid 97.65% w/w) were weighed into a glass vial equipped with a magnetic stirrer bar. 1.0 mL of sodium hydroxide standard solution 1.00 mol/L and 140 µl of 4-(2-hydroxy-ethyl)-morpholine were added and the mixture was sonicated to obtain an essentially clear solution. At ambient temperature, 1.0 mL ethanol was added followed by seeding with about three mg of crystalline monosodium salt. Then 2.0 mL ethanol was added and the seeding step was repeated. Upon seeding, a thick suspension was obtained that was diluted with 1.0 mL of an ethanol-water 2:1 mixture. After stirring at r.t. for about one hour the solid product was separated by filtration and after drying in air at r.t., characterized by powder X-ray diffraction (FIG. 1, Table 2), $^1$H-NMR, light microscopy and TG-FTIR. The yield was about 129 mg. The sample was further examined by HPLC, Raman spectroscopy, and IC-OES for determination of the sodium content. $^1$H-NMR shows that when the integral for the two protons of 5-methyl-(6S)-tetrahydrofolic acid near 7.6 is normalized to 2.0 the resultant integral for the six protons of the 4-(2-hydroxy-ethyl)-morpholine that appear near 3.7 is 5.96. This shows that the molar ratio of 5-methyl-(6S)-tetrahydrofolic acid to 4-(2-hydroxy-ethyl)-morpholine is essentially 1:1. Further analysis by TG-FTIR shows a water content of about 14 wt-%. The sodium content was determined by ICP-OES (inductively coupled plasma atomic emission spectroscopy) and a content of 3.2 wt-% sodium was found. This shows that the molar ratio of 5-methyl-(6S)-tetrahydrofolic acid to sodium is essentially 1:1. The product was further investigated by Raman spectroscopy FIG. 2, Table 1.

TABLE 1

Raman peaktable for the crystalline sodium salt of 5-methyl-(6S)-tetrahydrofolic acid and 4-(2-hydroxyethyl)-morpholine.

| wavenumber (cm$^{-1}$) | intensity (arbitrary units) |
|---|---|
| 2954 | 0.34 |
| 2875 | 0.23 |
| 1610 | 1.74 |
| 1582 | 0.40 |
| 1547 | 0.35 |
| 1482 | 0.23 |
| 1463 | 0.28 |
| 1419 | 0.19 |
| 1340 | 0.48 |
| 1293 | 0.50 |
| 1217 | 0.14 |
| 1184 | 0.31 |
| 1154 | 0.16 |
| 1069 | 0.12 |
| 1023 | 0.14 |
| 946 | 0.14 |
| 892 | 0.15 |
| 861 | 0.25 |
| 836 | 0.13 |
| 778 | 0.17 |
| 649 | 0.56 |
| 638 | 0.35 |
| 624 | 0.18 |
| 479 | 0.20 |
| 415 | 0.12 |
| 374 | 0.15 |

TABLE 2

PXRD peaktable the crystalline sodium salt of 5-methyl-(6S)-tetrahydrofolic acid and 4-(2-hydroxyethyl)-morpholine.

| °2-theta | d-spacings [Å] | intensity (qualitative) |
|---|---|---|
| 4.9 | 18.0 | w |
| 6.1 | 14.5 | vw |
| 8.3 | 10.7 | m |
| 9.8 | 9.0 | w |
| 10.7 | 8.3 | vw |
| 11.9 | 7.4 | w |
| 12.4 | 7.1 | w |
| 13.3 | 6.6 | w |
| 13.9 | 6.3 | s |
| 14.1 | 6.3 | vs |
| 14.2 | 6.2 | vs |
| 14.8 | 5.99 | w |
| 15.5 | 5.72 | s |
| 15.8 | 5.59 | vs |
| 16.2 | 5.47 | vs |
| 16.6 | 5.34 | vs |
| 17.0 | 5.21 | m |
| 17.5 | 5.05 | w |
| 18.2 | 4.86 | vs |
| 19.4 | 4.58 | m |
| 19.6 | 4.52 | s |
| 19.9 | 4.45 | vs |
| 20.1 | 4.41 | m |
| 20.8 | 4.27 | s |
| 21.0 | 4.23 | w |
| 21.4 | 4.15 | vw |
| 21.6 | 4.10 | w |
| 21.8 | 4.07 | vs |
| 22.1 | 4.02 | m |
| 22.4 | 3.97 | m |
| 22.8 | 3.90 | w |
| 23.6 | 3.76 | s |
| 23.9 | 3.72 | s |
| 24.3 | 3.66 | vw |
| 24.5 | 3.63 | w |
| 24.8 | 3.59 | m |
| 25.0 | 3.56 | vs |
| 25.2 | 3.53 | m |
| 25.5 | 3.49 | w |
| 25.9 | 3.43 | s |
| 26.6 | 3.35 | w |
| 26.8 | 3.33 | m |
| 27.3 | 3.26 | m |
| 27.8 | 3.21 | w |
| 28.1 | 3.17 | s |
| 28.5 | 3.13 | s |
| 28.6 | 3.11 | w |
| 28.9 | 3.08 | w |
| 29.6 | 3.02 | s |
| 30.8 | 2.90 | m |
| 33.5 | 2.67 | m |

Example 2: Kinetic Solubility of 5-methyl-(6S)-tetrahydrofolic Acid Sodium Salt Comprising 4-(2-hydroxyethyl)-morpholine 27.1 mg of crystalline 5-methyl-(6S)-tetrahydrofolic acid sodium salt containing 4-(2-hydroxy-ethyl)-morpholine (according to Example 1) with a stoichiometric ratio of 1:1:1 are weighed into a 4 ml glass vial with screw cap. 0.5 ml of purified/de-ionized water (for instance water for chromatography) is added. The mixture is vigorously agitated at room temperature and briefly sonicated and a clear slightly yellow solution is readily obtained (within a few seconds). Thus the solubility is greater than 54 mg per 1 ml of water. The solution remains clear for several hours at r.t.

Reference Example 3: Kinetic Solubility of the Calcium Salt of 5-methyl-(6S)-tetrahydrofolic Acid 27.9 mg of crystalline calcium salt of 5-methyl-(6S)-tetrahydrofolic acid (containing about 11% of water, thus corresponding to a dry weight of about 25 mg) are weighed into a 4 ml glass vial with screw cap. 2.535 ml of purified/de-ionized water (for instance water for chromatography) is added to the solid using an adjustable volumetric pipette. The mixture is vigorously agitated at room temperature and briefly sonicated. No clear solution can be obtained and a fairly concentrated suspension persists. Thus the kinetic solubility measured as described here is smaller than 10 mg per 1 ml of water.

Example 4: Microscopy of 5-methyl-(6S)-tetrahydrofolic Acid Sodium Salt Comprising 4-(2-hydroxyethyl)-morpholine A small aliquot (a few microliters) of the suspension obtained upon crystallization of the sodium salt of 5-methyl-(6S)-tetrahydrofolic acid comprising 4-(2-hydroxyethyl)-morpholine is transferred on a microscopy glass slide and examined with a light microscope from on Leitz Orthoplan under polarized light. A 10×10 magnification was applied. Microscopy shows rod shaped particles with lengths of up to about 100 μm and a thickness of about 10 to 20β. Such particles are easy to handle and have favorable filtration and drying properties. An image is shown in FIG. 4.

Reference Example 5: Microscopy of the Calcium Salt of 5-methyl-(6S)-tetrahydrofolic Acid A small aliquot (a few micrograms) of crystalline calcium salt of 5-methyl-(6S)-tetrahydrofolic acid is transferred on a microscopy glass slide and examined as dry powder with a light microscope under polarized light. A 10×10 magnification was applied. Microscopy shows large agglomerates that consist of a multitude of very small particles. Such particles are difficult to handle. An image is shown in FIG. 5.

Example 6: Preparation of a Crystalline Sodium Salt of 5-methyl-(6S)-tetrahydrofolic Acid Comprising 1-(2-hydroxyethyl)-pyrrolidine To 467 mg of 5-methyl-(6S)-tetrahydrofolic acid monohydrate (assay 5-methyltetrahydrofolic acid 97.65% w/w) were weighed into a glass vial equipped with a magnetic stirrer bar. 1.0 mL of sodium hydroxide standard solution 1.00 mol/L, then 126 μl of 1-(2-hydroxyethyl)-pyrrolidine and 4.0 mL ethanol were added. The resultant mixture was sonicated and stirred at ambient temperature for two hours. A thick suspension was obtained that was diluted with 2.0 mL of an ethanol-water mixture 4:1 v/v and stirring was continued for one hour before the solid product was separated by filtration. After drying in air at ambient temperature for half an hour the product was characterized by powder X-ray diffraction (FIG. 6, Table 3), H-NMR, and TG-FTIR. The yield was about 350 mg. The sample was further examined by HPLC and showed an HPLC purity of 99.16 area-%. H-NMR spectroscopy shows that when the integral for the two protons of 5-methyl-(6S)-tetrahydrofolic acid near 7.6 is normalized to 2.0, the resultant integral for the four methylene protons in the five-ring near 1.7 ppm of 1-(2-hydroxyethyl)-pyrrolidine is 4.2. This suggests that the molar ratio of 5-methyl-(6S)-tetrahydrofolic acid to 1-(2-hydroxyethyl)-pyrrolidine is essentially 1:1. Further analysis by TG-FTIR suggests a water content of about 9%. The sodium content was determined by ICP-OES (inductively coupled plasma atomic emission spectroscopy) and a content of 3.5 wt-% sodium was found. This shows that the molar ratio of 5-methyl-(6S)-tetrahydrofolic acid to sodium is essentially 1:1. The product was further investigated by Raman spectroscopy FIG. 7, Table 4.

TABLE 3

PXRD peaklist for sodium salt of 5-methyl-(6S)-tetrahydrofolic acid comprising 1-(2-hydroxyethyl)-pyrrolidine with 2-theta angles, d-spacing values in Ångstrom and qualitative intensity values as follows: vs = very strong, s = strong, m = medium, w = weak and vw = very weak.

| °2-theta | d-spacings [Å] | intensity (qualitative) |
|---|---|---|
| 4.8 | 18.2 | m |
| 8.3 | 10.6 | s |
| 11.9 | 7.5 | w |
| 12.5 | 7.1 | m |
| 13.6 | 6.5 | m |
| 14.3 | 6.2 | vs |
| 14.4 | 6.1 | vs |
| 15.6 | 5.68 | m |
| 16.0 | 5.54 | s |
| 16.1 | 5.51 | s |
| 16.7 | 5.29 | s |
| 17.0 | 5.22 | w |
| 18.3 | 4.84 | m |
| 18.5 | 4.79 | vs |
| 19.6 | 4.53 | m |
| 20.0 | 4.44 | s |
| 20.7 | 4.29 | m |
| 21.0 | 4.22 | w |
| 21.8 | 4.08 | s |
| 22.3 | 3.99 | w |
| 22.7 | 3.92 | w |
| 23.8 | 3.73 | w |
| 24.0 | 3.70 | m |
| 24.9 | 3.58 | m |
| 25.2 | 3.53 | vs |
| 25.5 | 3.49 | m |
| 25.8 | 3.45 | m |
| 26.1 | 3.41 | w |
| 26.7 | 3.33 | w |
| 27.1 | 3.29 | w |
| 27.8 | 3.21 | w |
| 28.4 | 3.14 | m |
| 29.7 | 3.01 | w |
| 30.1 | 2.96 | m |

TABLE 4

Raman data for the sodium salt of 5-methyl-(6S)-tetrahydrofolic acid comprising 1-(2-hydroxyethyl)-pyrrolidine with wavenumber in cm$^{-1}$ and intensity values. It should be noted that the intensities vary with Laser power, sample amount and other factors.

| wavenumber (cm$^{-1}$) | intensity (arbitrary units) |
|---|---|
| 3058 | 0.17 |
| 2954 | 0.46 |
| 2875 | 0.27 |
| 1611 | 2.10 |
| 1583 | 0.44 |
| 1548 | 0.47 |
| 1529 | 0.42 |
| 1480 | 0.28 |
| 1464 | 0.37 |
| 1419 | 0.26 |
| 1341 | 0.61 |
| 1295 | 0.60 |
| 1272 | 0.45 |
| 1216 | 0.16 |
| 1183 | 0.41 |

TABLE 4-continued

Raman data for the sodium salt of 5-methyl-(6S)-tetrahydrofolic acid comprising 1-(2-hydroxyethyl)-pyrrolidine with wavenumber in cm$^{-1}$ and intensity values. It should be noted that the intensities vary with Laser power, sample amount and other factors.

| wavenumber (cm$^{-1}$) | intensity (arbitrary units) |
|---|---|
| 1155 | 0.19 |
| 1068 | 0.15 |
| 947 | 0.18 |
| 890 | 0.21 |
| 861 | 0.27 |
| 836 | 0.16 |
| 779 | 0.15 |
| 648 | 0.71 |
| 637 | 0.44 |
| 624 | 0.22 |
| 480 | 0.24 |
| 416 | 0.15 |
| 375 | 0.18 |

Example 7: Kinetic Solubility of the Sodium Salt of 5-methyl-(6S)-tetrahydrofolic Acid Comprising 1-(2-hydroxyethyl)-pyrrolidine 78.5 mg of crystalline sodium salt of 5-methyl-(6S)-tetrahydrofolic acid comprising 1-(2-hydroxyethyl)-pyrrolidine is weighed into a 4 ml glass vial with screw cap. Then 0.785 ml of purified/de-ionized water is added. The mixture is agitated at room temperature and a clear solution is readily obtained (within a few seconds). Thus the solubility is greater than 100 mg per 1 ml of water. The solution remains clear for several hours at r.t.

Example 8: Preparation of a Crystalline Sodium Salt of 5-methyl-(6S)-tetrahydrofolic Acid Comprising 2-dimethylaminoethanol 467 mg of 5-methyl-(6S)-tetrahydrofolic acid monohydrate (assay 5-methyltetrahydrofolic acid 97.65% w/w) were weighed into a glass vial equipped with a magnetic stirrer bar. The added 1.0 mL of sodium hydroxide standard solution 1.00 mol/L, then added 110 μl of 2-dimethylaminoethanol (~1.1 equivalents). To the essentially clear solution 2.0 mL of ethanol was added. The resultant mixture was sonicated, seeded with crystalline salt, and stirred at ambient temperature for one hour. A thick suspension was obtained that was diluted with 2.0 mL of an ethanol-water mixture 4:1 v/v and stirring was continued for one hour before the solid product was separated by filtration and after drying in air at r.t. The crystalline product was characterized by H-NMR, Raman spectroscopy, PXRD, and TG-FTIR. Powder X-ray diffraction shows that the sample is clearly crystalline in nature (FIG. 8, Table 5). H-NMR spectroscopy shows that when the integral for the two protons of 5-methyl-(6S)-tetrahydrofolic acid near 7.6 is normalized to 2.0, the resultant integral for the six protons of the two methyl groups 2-dimethylaminoethanol near 2.1 ppm of is 6.6. This suggests that the molar ratio of 5-methyl-(6S)-tetrahydrofolic acid to 2-dimethylaminoethanol is essentially 1:1. The sample was further examined by Raman spectroscopy and it shows a Raman spectrum as described in Table 6 and shown in FIG. 9. The sodium content was determined by ICP-OES (inductively coupled plasma atomic emission spectroscopy) and a content of 3.2 wt-% sodium was found. Further analysis by TG-FTIR suggests a water content of about 10%.

Based on the two results, the product has a 1:1 molar ratio of 5-methyl-(6S)-tetrahydrofolic acid to sodium.

TABLE 5

PXRD peaklist for sodium salt of 5-methyl-(6S)-tetrahydrofolic acid comprising 2-dimethylaminoethanol with 2-theta angles, d-spacing values in Ångstrom and qualitative intensity values as follows: vs = very strong, s = strong, m = medium, 32 weak and vw = very weak.

| °2-theta | d-spacings [A] | intensity (qualitative) |
|---|---|---|
| 4.8 | 18.4 | w |
| 8.3 | 10.6 | s |
| 11.8 | 7.5 | w |
| 12.5 | 7.1 | w |
| 13.6 | 6.5 | s |
| 14.2 | 6.2 | vs |
| 14.4 | 6.1 | s |
| 15.7 | 5.66 | m |
| 15.8 | 5.59 | s |
| 16.0 | 5.52 | m |
| 16.7 | 5.30 | s |
| 17.1 | 5.19 | m |
| 17.3 | 5.12 | w |
| 18.5 | 4.80 | vs |
| 19.8 | 4.49 | s |
| 19.9 | 4.45 | s |
| 20.8 | 4.27 | w |
| 21.0 | 4.22 | w |
| 21.9 | 4.06 | m |
| 22.1 | 4.02 | w |
| 22.7 | 3.92 | m |
| 23.7 | 3.75 | w |
| 24.0 | 3.70 | s |
| 25.1 | 3.54 | s |
| 25.5 | 3.49 | m |
| 25.9 | 3.44 | m |
| 26.8 | 3.33 | w |
| 26.9 | 3.31 | w |
| 27.2 | 3.28 | w |
| 27.8 | 3.20 | m |
| 28.5 | 3.13 | m |
| 29.6 | 3.02 | w |
| 29.9 | 2.98 | w |
| 30.2 | 2.96 | s |

TABLE 6

Raman data for the sodium salt of 5-methyl-(6S)-tetrahydrofolic acid comprising 2-dimethylaminoethanol with wavenumber in cm$^{-1}$ and intensity values. It should be noted that the intensities vary with Laser power, sample amount and other factors.

| wavenumber (cm$^{-1}$) | intensity (arbitrary units) |
|---|---|
| 3054 | 0.08 |
| 2955 | 0.16 |
| 2871 | 0.10 |
| 1609 | 0.91 |
| 1580 | 0.27 |
| 1552 | 0.27 |
| 1463 | 0.20 |
| 1420 | 0.14 |
| 1345 | 0.33 |
| 1307 | 0.34 |
| 1272 | 0.27 |
| 1183 | 0.21 |
| 1059 | 0.08 |
| 1023 | 0.07 |
| 948 | 0.08 |
| 890 | 0.10 |
| 864 | 0.15 |
| 836 | 0.09 |
| 777 | 0.10 |
| 649 | 0.30 |
| 637 | 0.20 |
| 480 | 0.11 |

TABLE 6-continued

Raman data for the sodium salt of 5-methyl-(6S)-tetrahydrofolic acid comprising 2-dimethylaminoethanol with wavenumber in cm$^{-1}$ and intensity values. It should be noted that the intensities vary with Laser power, sample amount and other factors.

| wavenumber (cm$^{-1}$) | intensity (arbitrary units) |
|---|---|
| 414 | 0.08 |
| 372 | 0.09 |

Example 9: Kinetic Solubility of the Sodium Salt of 5-methyl-(6S)-tetrahydrofolic Acid Comprising 2-dimethylaminoethanol 55 mg of crystalline sodium salt of 5-methyl-(6S)-tetrahydrofolic acid comprising 2-dimethylaminoethanol is weighed into a 4 ml glass vial with screw cap. Then 1.0 ml of purified/de-ionized water is added. The mixture is agitated at room temperature and a clear solution is readily obtained (within a few seconds). Thus the solubility is greater than 55 mg per 1 ml of water. The solution remains clear for several hours at r.t.

Example 10: Preparation of the Crystalline 1:1:1 Salt of 5-methyl-(6S)-tetrahydrofolic Acid, Sodium and 4-(2-hydroxyethyl)-morpholine Starting from 5-methyl-(6S)-tetrahydrofolic Acid To a mixture of 40 g 5-methyl-(6S)-tetrahydrofolic acid (assay 5-methyltetrahydrofolic acid 95.42% w/w) and 86 g water 3.46 g solid sodium hydroxide and 21.79 g 4-(2-hydroxyethyl) morpholine were added at room temperature under a nitrogen atmosphere while stirring. The mixture was added within 5.5 hours to a mixture of 472 g ethanol with 5% v/v 2-propanol and 0.4 g crystalline sodium salt of 5-methyl-(6S)-tetrahydrofolic acid at 23° C. while stirring. 3 g water were added and the mixture was stirred for an additional hour at 23° C. The solids were separated by filtration, washed three times with each 133 mL ethanol 5% 2-propanol/water 1:7 v/v and dried in vacuum at 40° C. for 16.5 hours to give 46.07 g of an off-white powder corresponding to 85% yield (assay 5-methyltetrahydrofolic acid 70.6% w/w). PXRD confirmed the crystalline nature of the sample. $^1$H-NMR shows that when the integral for the two protons of 5-methyl-(6S)-tetrahydrofolic acid near 7.6 is normalized to 2.0 the resultant integral for the six protons of the 4-(2-hydroxy-ethyl)-morpholine that appear near 3.7 is 5.96. This shows that the molar ratio of 5-methyl-(6S)-tetrahydrofolic acid to 4-(2-hydroxy-ethyl)-morpholine is essentially 1:1. Further investigation by TGA (Thermogravimetric Analysis) revealed a mass loss of about 5.58%. The sodium content found by IC (Ion chromatography) was 3.5%. This shows that the molar ratio of 5-methyl-(6S)-tetrahydrofolic acid to sodium is essentially 1:1. HPLC showed a purity of 98.2%.

The invention claimed is:

1. A crystalline salt of 5-methyl-(6S)-tetrahydrofolic acid, comprising
   (i) 5-methyl-(6S)-tetrahydrofolic acid,
   (ii) sodium and
   (iii) an organic base having a pKa value of 6 to 11;
   wherein the molar ratio of 5-methyl-(6S)-tetrahydrofolic acid to the sodium is 1:0.5 to 1:1.5 and the molar ratio of 5-methyl-(6S)-tetrahydrofolic acid to the organic base is 1:0.5 to 1:1.5;
   or a hydrate or solvate thereof.

2. The crystalline salt of claim 1, wherein the molar ratio of 5-methyl-(6S)-tetrahydrofolic acid to the sodium is 1:0.75 to 1:1.25 and the molar ratio of 5-methyl-(6S)-tetrahydrofolic acid to the organic base is 1:0.75 to 1:1.25.

3. The crystalline salt of claim 1, wherein the molar ratio of 5-methyl-(6S)-tetrahydrofolic acid to the sodium is approximately 1:1 and the molar ratio of 5-methyl-(6S)-tetrahydrofolic acid to the organic base is approximately 1:1.

4. A crystalline salt of claim 1, wherein the organic base having a pKa value of 6 to 11 is 4-(2-hydroxyethyl)-morpholine, 1-(2-hydroxyethyl)-pyrrolidine, imidazole, 2-dimethylaminoethanol, or tert-butylamine; or is a mixture thereof.

5. The crystalline salt of claim 1, wherein the organic base is 4-(2-hydroxyethyl)-morpholine and which crystalline salt has a PXRD pattern with at least one characteristic peak, which is expressed in 2θ±0.2° 2θ with CuKα radiation, at 14.1, 15.8, 16.2, 16.6, 18.2, 19.9, 21.8, and/or 25.0.

6. The crystalline salt of claim 1, wherein the organic base is 4-(2-hydroxyethyl)-morpholine and which crystalline salt has a PXRD pattern with at least one characteristic peak, which is expressed in 2θ±0.2° 2θ with CuKα radiation, at 8.3, 13.9, 14.1, 14.2, 15.5, 15.8, 16.2, 16.6, 18.2, 19.4, 19.6, 19.9, 20.1, 20.8, 21.8, 23.6, 23.9, 25.0, 25.9, 28.1, 28.5, and/or 29.6.

Figure 1:
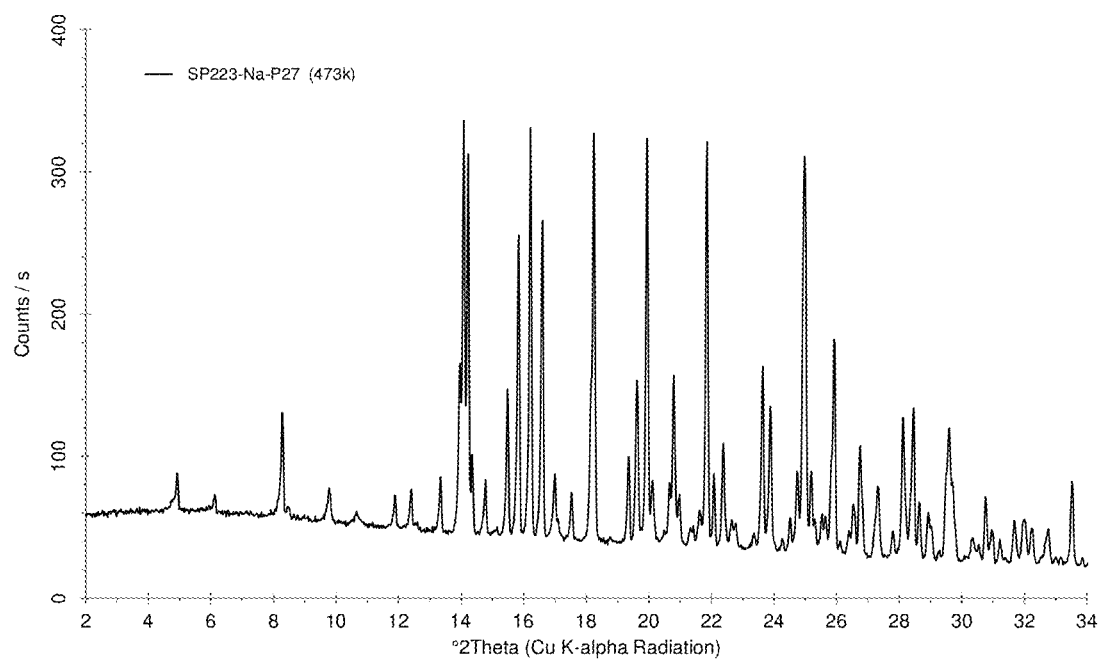
FIG. 1: PXRD of the crystalline sodium salt of 5-methyl-(6S)-tetrahydrofolic acid comprising 4-(2-hydroxyethyl)-morpholine according to Example 1.
Figure 2:
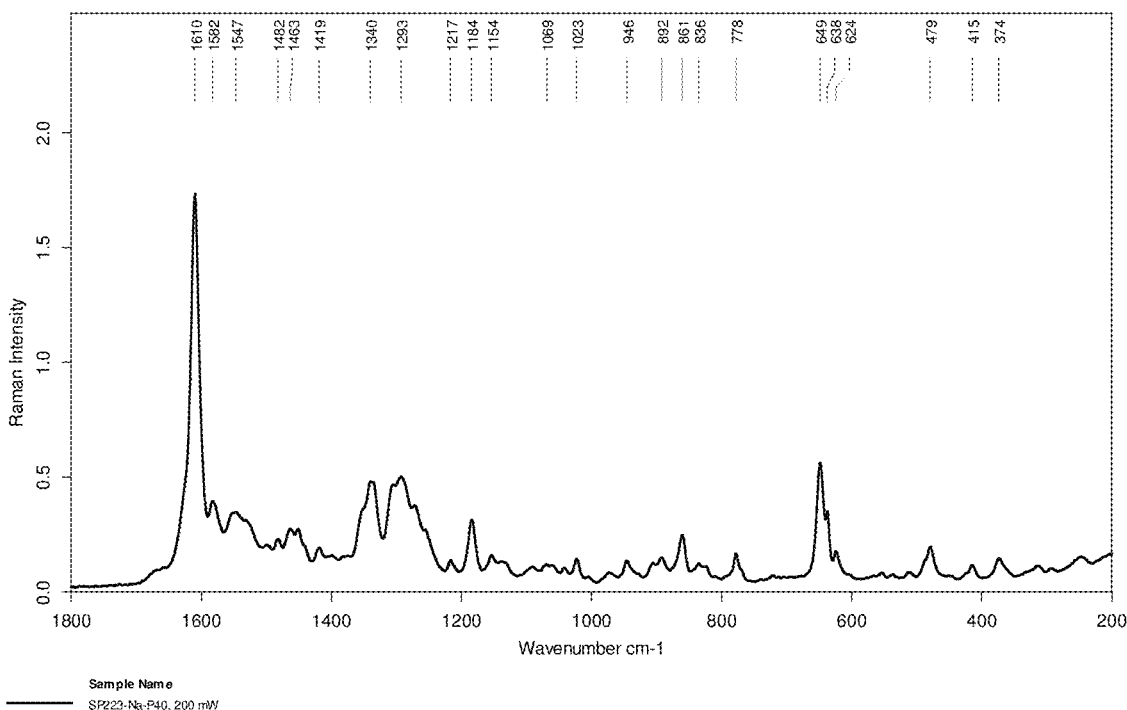
FIG. 2: Raman spectrum of the crystalline sodium salt of 5-methyl-(6S)-tetrahydrofolic acid comprising 4-(2-hydroxyethyl)-morpholine according to Example 1.
Figure 3:
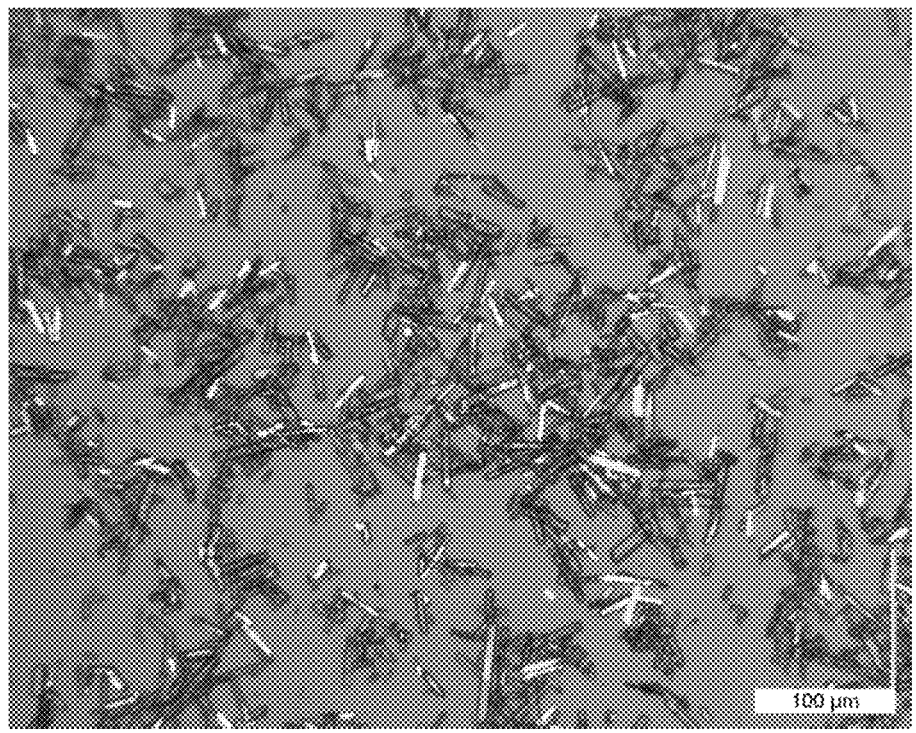
FIG. 3: Microscopy image of sodium salt of 5-methyl-(6S)-tetrahydrofolic acid comprising 4-(2-hydroxyethyl)-morpholine according to Example 1.
Figure 4:
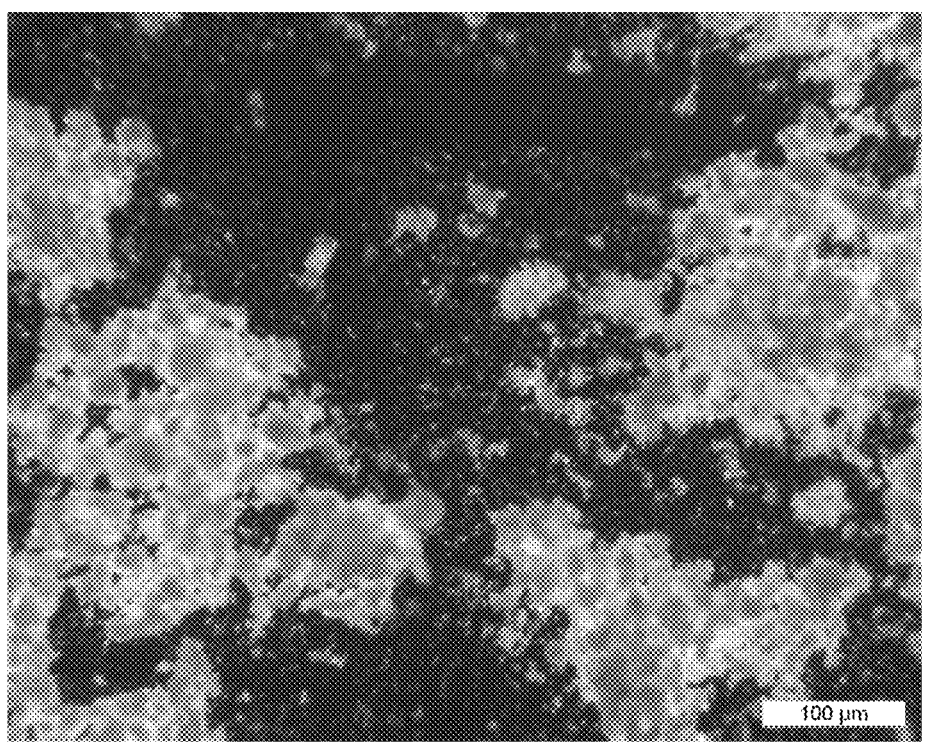
FIG. 4: Microscopy image of calcium salt of 5-methyl-(6S)-tetrahydrofolic acid (dry powder sample).
Figure 5:
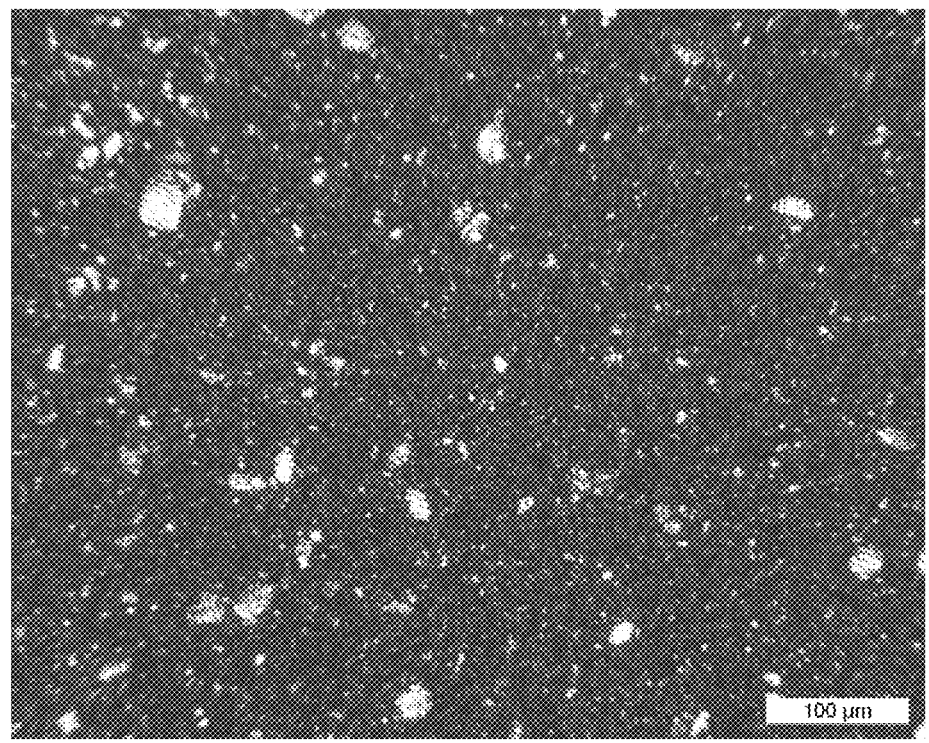
FIG. 5: Microscopy image of calcium salt of 5-methyl-(6S)-tetrahydrofolic acid (dispersed in paraffin oil).

7. The crystalline salt of claim 1, wherein the organic base is 4-(2-hydroxyethyl)-morpholine and which crystalline salt has a PXRD pattern substantially as shown in FIG. 1.

8. The crystalline salt of claim 1, wherein the organic base is 1-(2-hydroxyethyl)-pyrrolidine and which crystalline salt has a PXRD pattern with at least one characteristic peak, which is expressed in 2θ±0.2° 2θ with CuKα radiation, at 8.3, 14.3, 14.4, 15.6, 16.0, 16.7, 18.5, 20.0, 21.8, and/or 25.2.

9. The crystalline salt of claim 8, wherein the organic base is 1-(2-hydroxyethyl)-pyrrolidine and which crystalline salt has a PXRD pattern with at least one characteristic peak, which is expressed in 2θ±0.2° 2θ with CuKα radiation, at 4.8, 8.3, 12.5, 13.6, 14.3, 14.4, 15.6, 16.0, 16.1, 16.7, 18.3, 18.5, 19.6, 20.0, 20.7, 21.8, 22.3, 22.7, 23.8, 24.0, and/or 25.2.

Figure 6:
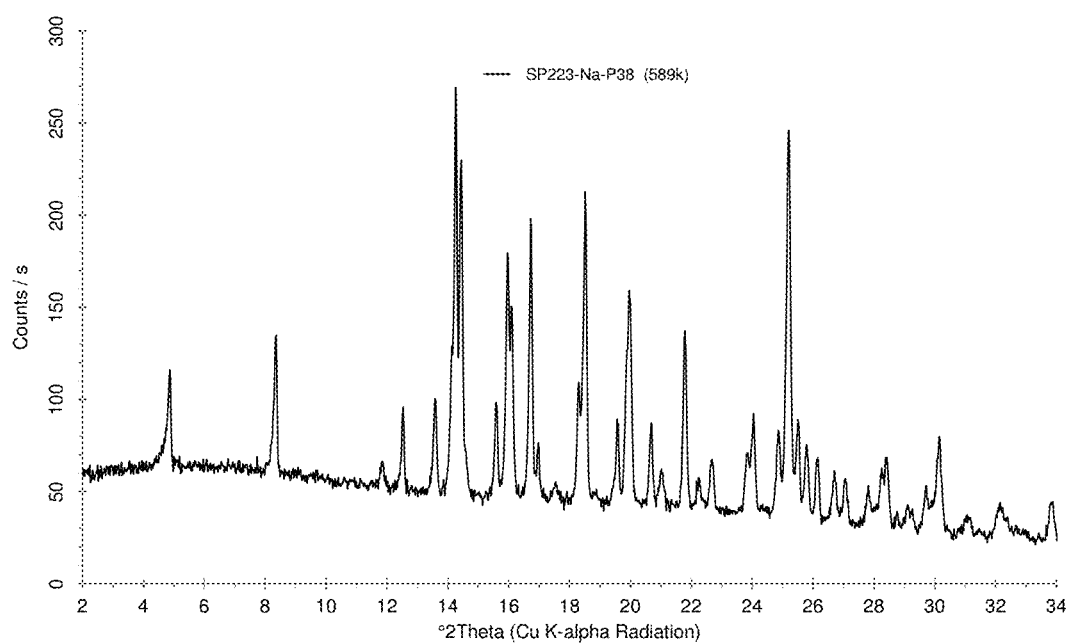
FIG. 6: PXRD pattern of the crystalline sodium salt of 5-methyl-(6S)-tetrahydrofolic acid comprising 1-(2-hydroxyethyl)-pyrrolidine according to Example 6
Figure 7:
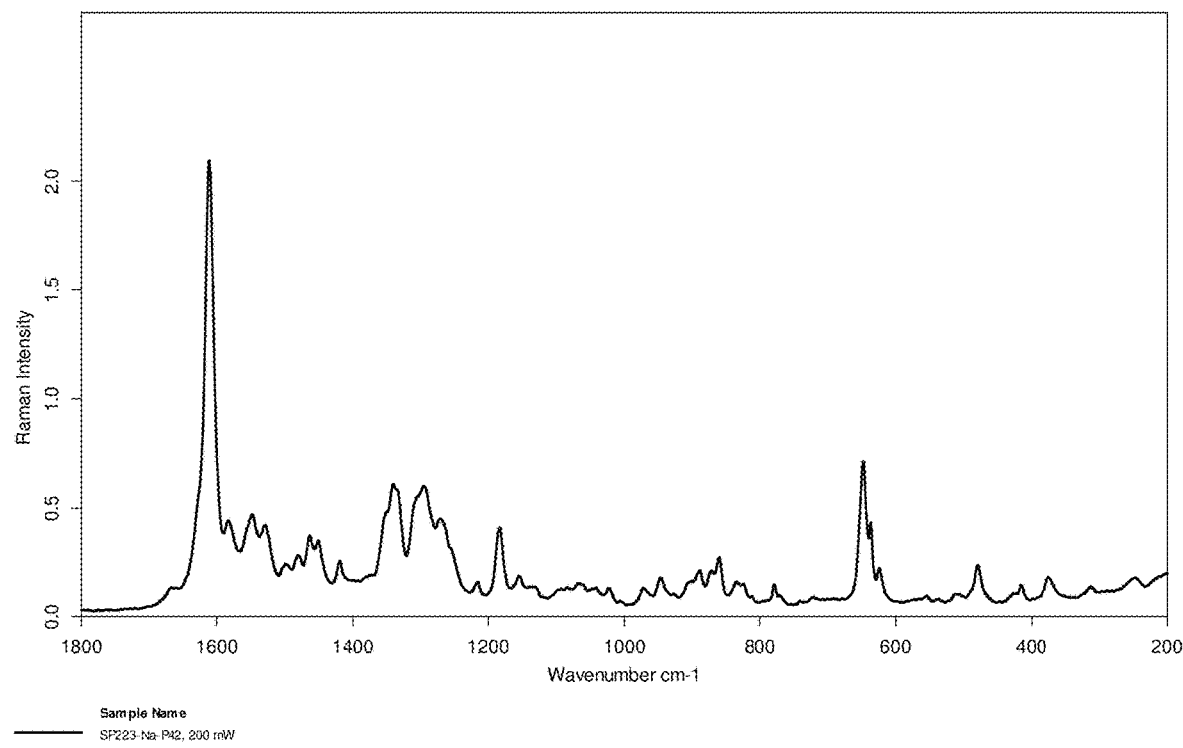
FIG. 7: Raman spectrum of the crystalline sodium salt of 5-methyl-(6S)-tetrahydrofolic acid comprising 1-(2-hydroxyethyl)-pyrrolidine according to Example 6

10. The crystalline salt of claim 8, wherein the organic base is 1-(2-hydroxyethyl)-pyrrolidine and which crystalline salt has a PXRD pattern substantially as shown in FIG. 6.

11. The crystalline salt of claim 1, wherein the organic base is 2-dimethylaminoethanol and which crystalline salt has a PXRD pattern with at least one characteristic peak, which is expressed in 2θ±0.2° 2θ with CuKα radiation, at 8.3, 13.6, 14.2, 14.4, 15.8, 16.7, 18.5, 19.8, 19.9, 24.0, 25.1, and/or 30.2.

12. The crystalline salt of claim 11, wherein the organic base is 2-dimethylaminoethanol and which crystalline salt has a PXRD pattern with at least one characteristic peak, which is expressed in 2θ±0.2° 2θ with CuKα radiation, at 8.3, 13.6, 14.2, 14.4, 15.7, 15.8, 16.0, 16.7, 17.1, 18.5, 19.8, 19.9, 21.9, 22.1, 22.7, 24.0, 25.1, 25.5, 25.9, 27.8, 28.5 and/or 30.2.

Figure 8:
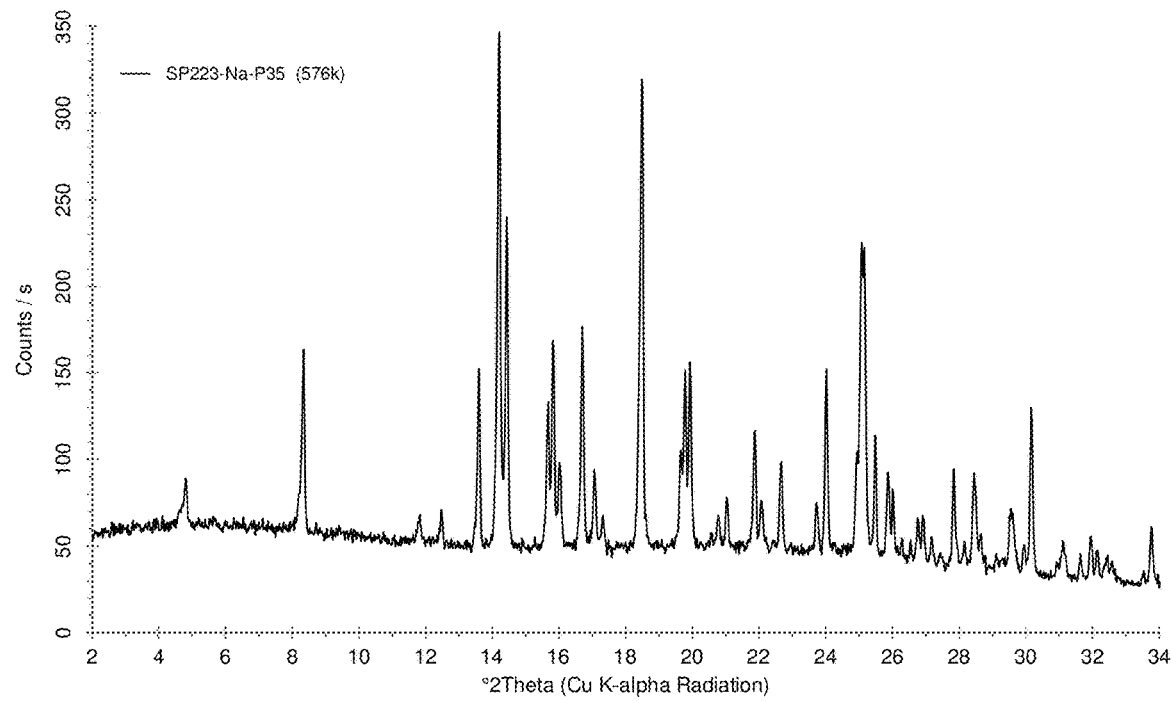
FIG. 8: PXRD pattern of the crystalline sodium salt of 5-methyl-(6S)-tetrahydrofolic acid comprising 2-dimethylaminoethanol according to Example 8
Figure 9:
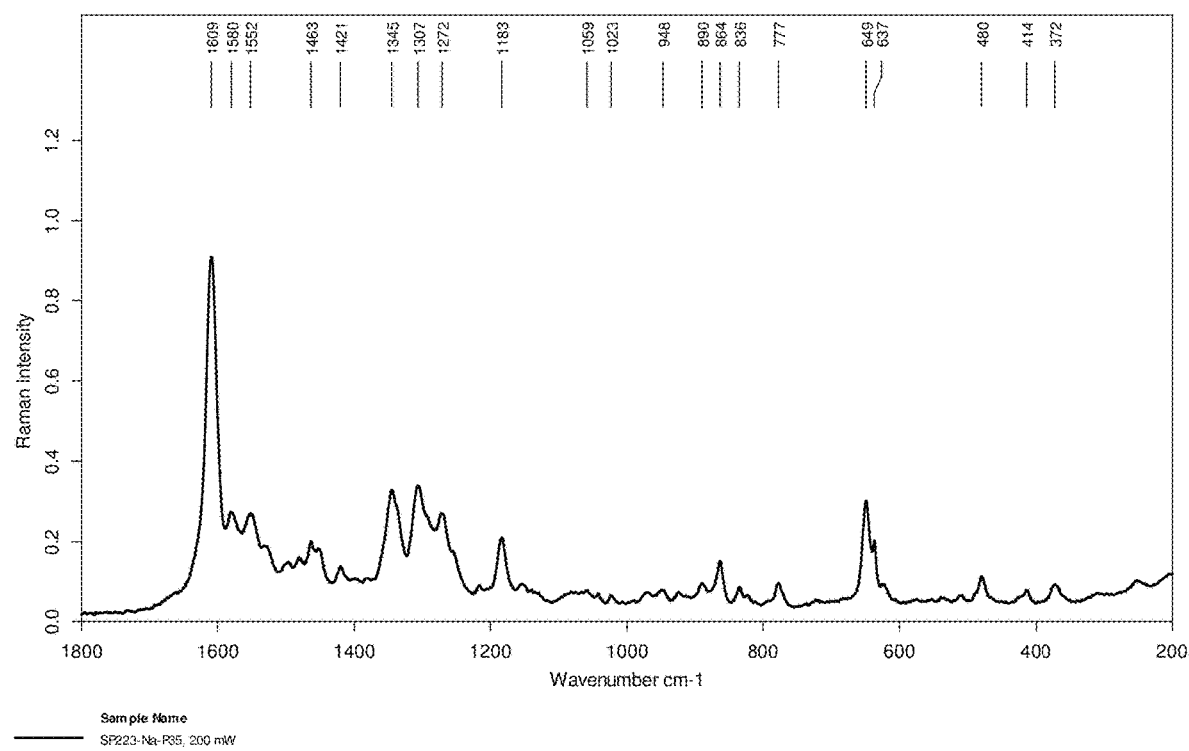
FIG. 9: Raman spectrum of the crystalline sodium salt of 5-methyl-(6S)-tetrahydrofolic acid comprising 2-dimethylaminoethanol according to Example 8

13. The crystalline salt of claim 11, wherein the organic base is 2-dimethylaminoethanol and which crystalline salt has a PXRD pattern substantially as shown in FIG. 8.

14. The crystalline sodium salt of 5-methyl-(6S)-tetrahydrofolic acid according to claim 1, having at least 99% or more chemical and stereoisomerical purity.

15. A process for obtaining the crystalline sodium salt according to claim 1, comprising the steps of:
 a) providing 5-methyl-(6S)-tetrahydrofolic acid, optionally in a solvent or a mixture of solvents;
 b) adding sodium hydroxide;
 c) adding an organic base having a pKa value of 6 to 11; wherein the order of steps b) and c) may be interchanged;
 d) optionally adding a solvent or a mixture of solvents to the resultant composition of step b) or step c);
 e) crystallizing;
 f) optionally adding more solvent or mixture of solvents; and
 g) isolating obtained solid.

16. The process of claim 15, wherein the 5-methyl-(6S)-tetrahydrofolic acid and sodium hydroxide are present at a molar ratio in step b) in the range of 1:0.5 to 1:1.5.

17. The process of claim 15, wherein the organic base of step c) is 4-(2-hydroxyethyl)-morpholine, 1-(2-hydroxyethyl)-pyrrolidine, imidazole, 2-dimethylaminoethanol, or tert-butylamine; or is a mixture thereof.

18. A pharmaceutical composition, food additive, vitamin and/or other preparation comprising the crystalline salt of 5-methyl-(6S)-tetrahydrofolic according to claim 1 and one or more acceptable excipients suitable for forming said pharmaceutical composition, food additive, vitamin and/or other preparation.

19. The pharmaceutical composition according to claim 18, which is in the form of a tablet, capsule, oral liquid preparation, powder, lyophilisate, granule, lozenge, reconstitutable powder, injectable or infusable solution or suspension, or suppository.

20. A method for the treatment in homocysteine-lowering, of anemia, neural tube defects, cardiovascular diseases, depression, cognitive impairment, Alzheimer's disease, osteoporosis and/or dietary management of low plasma and/or low red blood cell and/or low cerebrospinal fluid and/or low peripheral or central nervous system folate, comprising administering to a subject in need thereof a crystalline salt of claim 1.

21. The process of claim 15, wherein the 5-methyl-(6S)-tetrahydrofolic acid and organic base are present at a molar ratio in step c) in the range of 1:0.5 to 1:3.

22. The process of claim 15, wherein the solvent and/or mixture of solvents according to step a), d) and/or f) is selected from the group consisting of water, water-soluble alcohols, methanol, ethanol, isopropanol, n-propanol, acetonitrile, tetrahydrofuran, acetone, methyl ethyl ketone, methyl isobutyl ketone, benzylalcohol, and mixtures thereof.

23. The process of claim 15, wherein steps b) and c) are interchanged.

24. The process of claim 15, wherein in step c), d) and/or e) the temperature is less than 60° C.

25. The process of claim 15, wherein in step a), b), c), d) and/or e) seed crystals are added.

26. The pharmaceutical composition according to claim 18, further comprising at least one additional therapeutic agent.

27. The pharmaceutical composition according to claim 18, which is a pharmaceutical composition for oral, parenteral, intramuscular, intraspinal, intrathecal, peridontal, topical or rectal administration.

28. The crystalline salt of claim 1, wherein the organic base is 4-(2-hydroxyethyl)-morpholine and which crystalline salt has a PXRD pattern with characteristic peaks, which are expressed in 2θ±0.2° 2θ with CuKα radiation, at 14.1, 15.8, 16.2, 16.6, 18.2, 19.9, 21.8, and 25.0.

29. A crystalline salt of 5-methyl-(6S)-tetrahydrofolic acid, comprising
 (i) 5-methyl-(6S)-tetrahydrofolic acid,
 (ii) sodium and
 (iii) an organic base having a pKa value of 6 to 11;
 wherein the molar ratio of 5-methyl-(6S)-tetrahydrofolic acid to the sodium is 1:0.5 to 1:1.5 and the molar ratio of 5-methyl-(6S)-tetrahydrofolic acid to the organic base is 1:0.5 to 1:1.5.

* * * * *